United States Patent
Ollmar et al.

(10) Patent No.: US 9,636,035 B2
(45) Date of Patent: May 2, 2017

(54) MEDICAL APPARATUS FOR DETERMINATION OF BIOLOGICAL CONDITIONS USING IMPEDANCE MEASUREMENTS

(75) Inventors: Stig Ollmar, Huddinge (SE); Ulrik Birgersson, Stockholm (SE); Peter Aberg, Hagersten (SE); Ingrid Nicander, Stockholm (SE); Thierry Corman, Sollentuna (SE)

(73) Assignee: SCIBASE AB, Stockholm (SE)

( * ) Notice: Subject to any disclaimer, the term of this patent is extended or adjusted under 35 U.S.C. 154(b) by 1291 days.

(21) Appl. No.: 11/302,498

(22) Filed: Dec. 14, 2005

(65) Prior Publication Data

US 2007/0135729 A1    Jun. 14, 2007

(51) Int. Cl.
  A61B 5/05     (2006.01)
  A61B 5/053    (2006.01)
  A61B 5/00     (2006.01)

(52) U.S. Cl.
  CPC .......... *A61B 5/0531* (2013.01); *A61B 5/411* (2013.01); *A61B 5/444* (2013.01); *A61B 5/685* (2013.01)

(58) Field of Classification Search
  CPC .............................. A61B 5/0531; A61B 5/685
  USPC ......... 600/372–373, 393, 547, 548; 607/115, 607/116
  See application file for complete search history.

(56) References Cited

U.S. PATENT DOCUMENTS 4,004,578 A    1/1977 Palmius
5,036,861 A    8/1991 Sembrowich et al.
5,115,133 A    5/1992 Knudson
(Continued)

FOREIGN PATENT DOCUMENTS

CN    1494876       5/2004
EP    1 437 091     7/2004
(Continued)

OTHER PUBLICATIONS

Translation of Taiwanese official action, Oct. 7, 2009, in corresponding Taiwanese Application No. 095146871.
(Continued)

*Primary Examiner* — Rene Towa
*Assistant Examiner* — H. Q. Nguyen
(74) *Attorney, Agent, or Firm* — Birch, Stewart, Kolasch & Birch, LLP

(57) ABSTRACT

Medical apparatus for diagnosing of a diseased condition of the skin of a subject. The apparatus comprises an electrically conducting probe including a plurality of electrodes, each electrode comprising a plurality of micro-needles, wherein each electrode comprises a base substrate, said micro-needles being integrally formed with said substrate and arranged in a laterally spaced relationship apart from each other and having a length being sufficient to penetrate the stratum corneum, said micro-needles being arranged with an at least partially oblique shape. Furthermore, the present invention relates to an electrode for use in the device, arrays of micro-needle and method for the diagnostics of biological conditions using impedance measurements. The diagnostics is in particular related to cancer, and preferably skin cancer, wherein skin cancer is a basal cell carcinoma, a malignant melanoma, a squamous cell carcinoma, or precursors of such lesions.

31 Claims, 12 Drawing Sheets

(56) References Cited

U.S. PATENT DOCUMENTS

| | | |
|---|---|---|
| 5,146,091 A | 9/1992 | Knudson |
| 5,197,951 A | 3/1993 | Mahurkar |
| 5,222,496 A | 6/1993 | Clarke et al. |
| 5,433,197 A | 7/1995 | Stark |
| 6,334,856 B1* | 1/2002 | Allen et al. .................. 604/191 |
| 6,334,865 B1 | 1/2002 | Redmond et al. |
| 6,451,240 B1* | 9/2002 | Sherman et al. ............. 264/504 |
| 6,652,478 B1* | 11/2003 | Gartstein et al. ............... 604/22 |
| 6,743,211 B1 | 6/2004 | Prausnitz et al. |
| 2002/0082543 A1* | 6/2002 | Park et al. ..................... 604/21 |
| 2002/0138049 A1* | 9/2002 | Allen et al. .................. 604/272 |
| 2003/0009113 A1 | 1/2003 | Olson |
| 2003/0050548 A1 | 3/2003 | Schmidt et al. |
| 2003/0050550 A1 | 3/2003 | Schmidt et al. |
| 2003/0078482 A1 | 4/2003 | Kenan et al. |
| 2003/0083645 A1 | 5/2003 | Angel et al. |
| 2003/0236543 A1* | 12/2003 | Brenneman et al. ......... 606/181 |
| 2004/0243063 A1 | 12/2004 | Roy et al. |
| 2005/0209565 A1* | 9/2005 | Yuzhakov et al. ........... 604/173 |

FOREIGN PATENT DOCUMENTS

| | | |
|---|---|---|
| EP | 1 437 091 A1 | 7/2004 |
| EP | 1 600 104 | 11/2005 |
| TW | 512067 | 12/2002 |
| WO | WO-92/06634 | 4/1992 |
| WO | WO-95/04496 | 2/1995 |
| WO | WO-98/04190 | 2/1998 |
| WO | WO-99/39627 | 8/1999 |
| WO | WO-01/26338 A2 | 4/2001 |
| WO | WO 01/52731 | 7/2001 |
| WO | WO 2007/068433 | 6/2007 |

OTHER PUBLICATIONS

ROC (Taiwan) Search Report mailed Sep. 14, 2009 in corresponding Taiwanese Application No. 095146871.

International Search Report mailed Aug. 10, 2007 in corresponding PCT Application PCT/EP2006/011924.

* cited by examiner

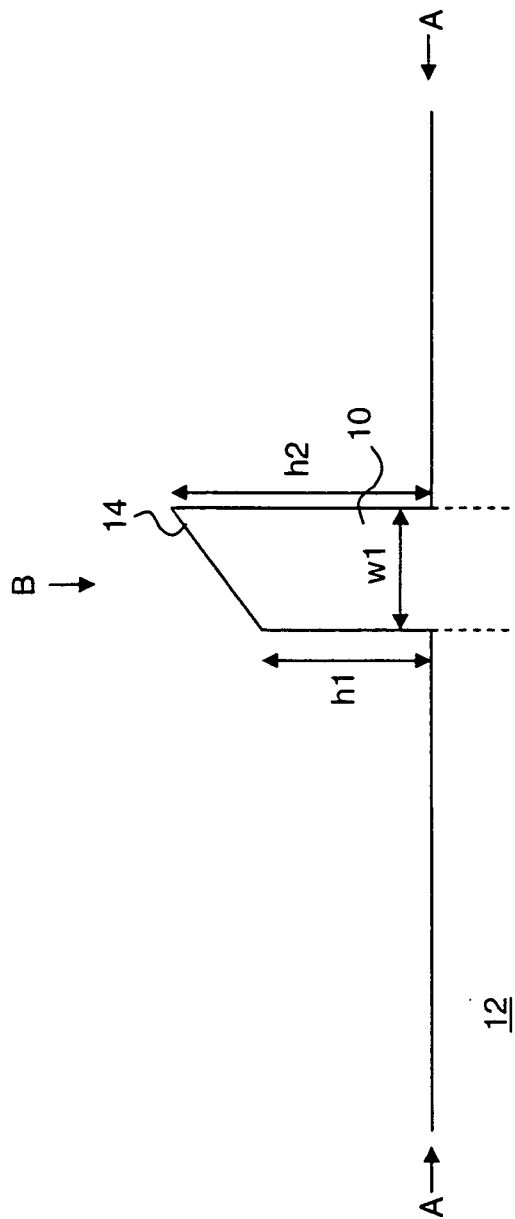
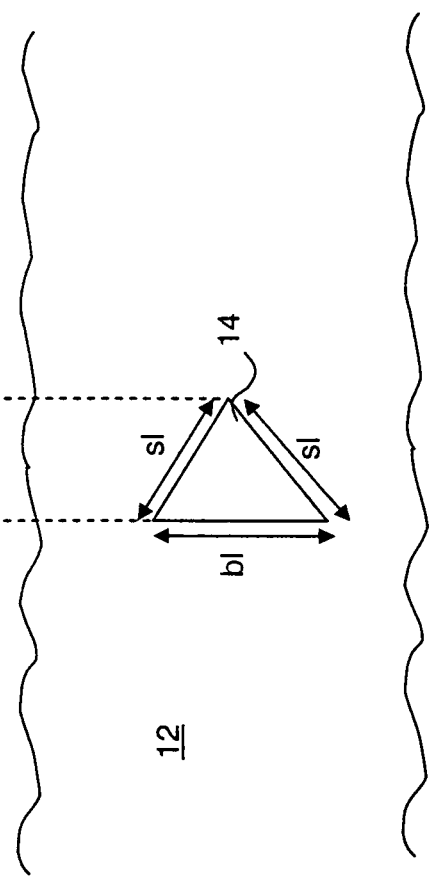

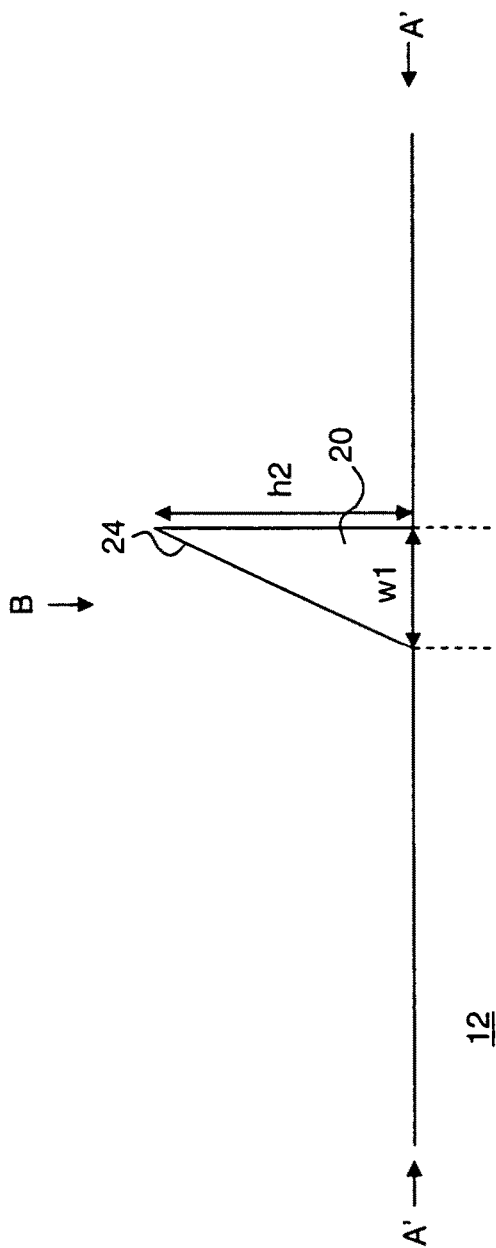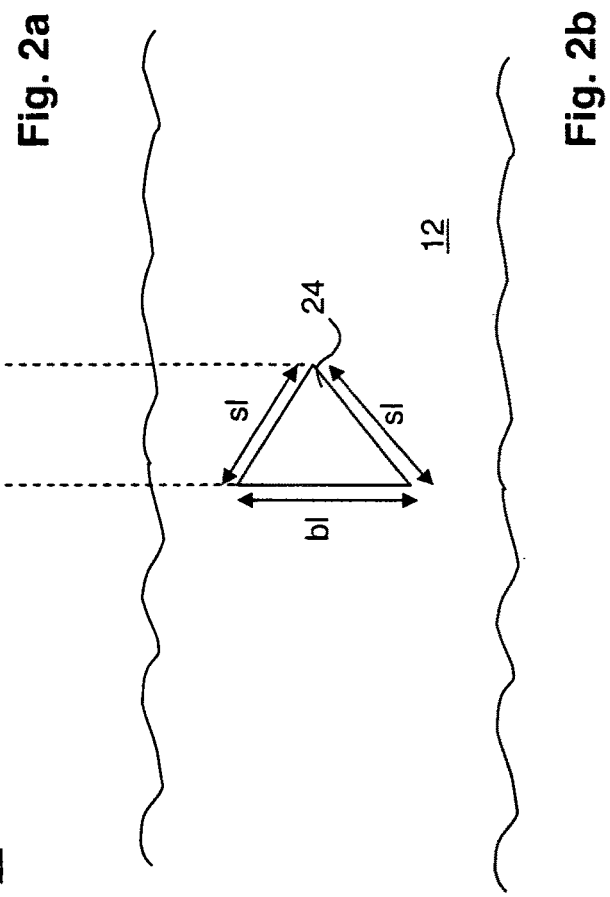

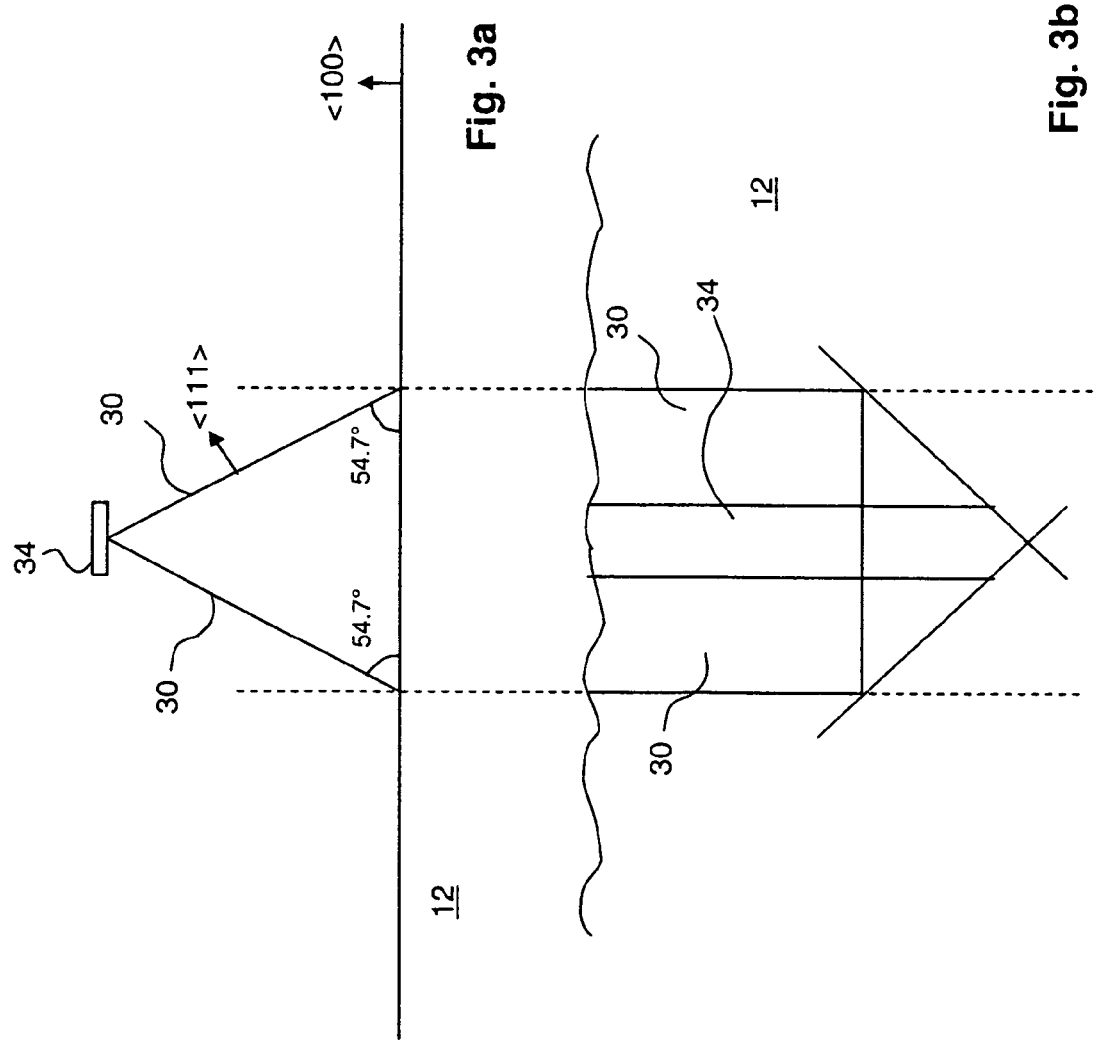

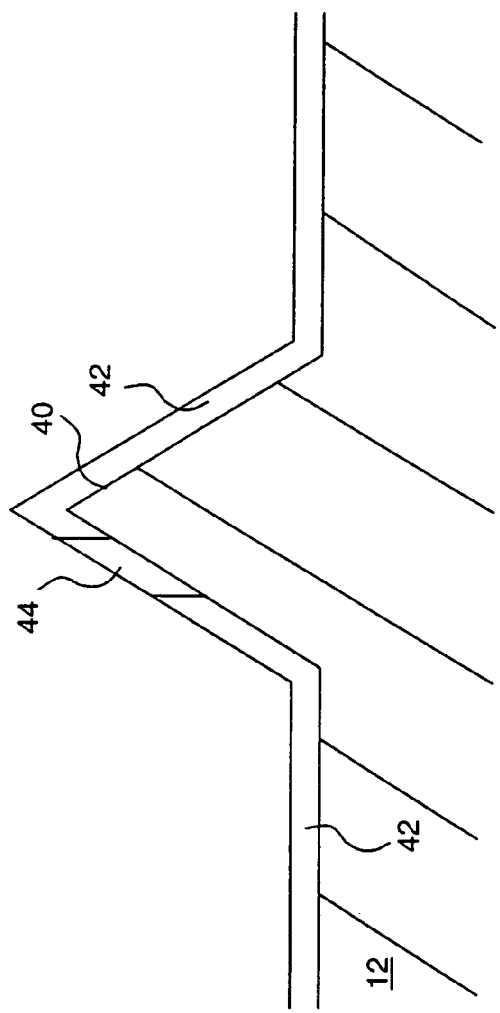
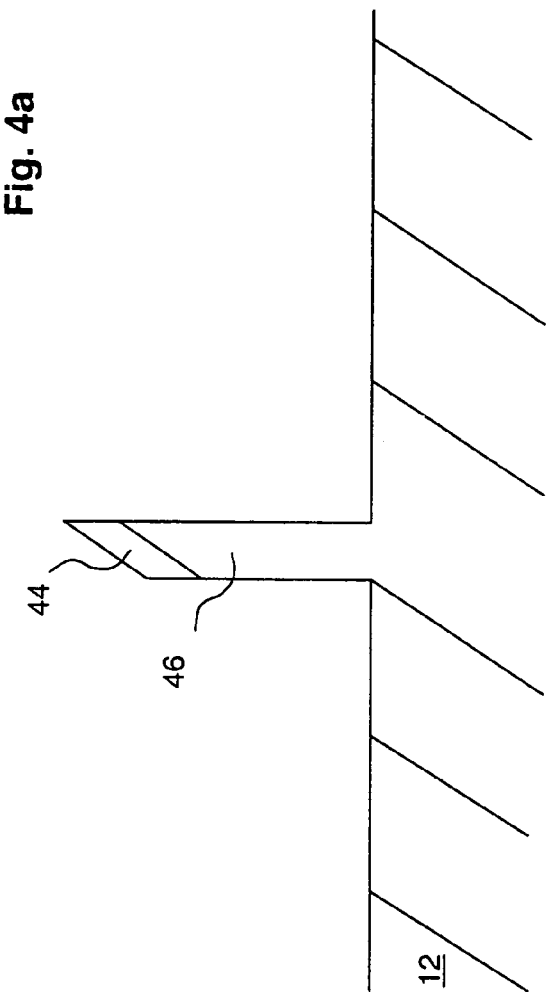

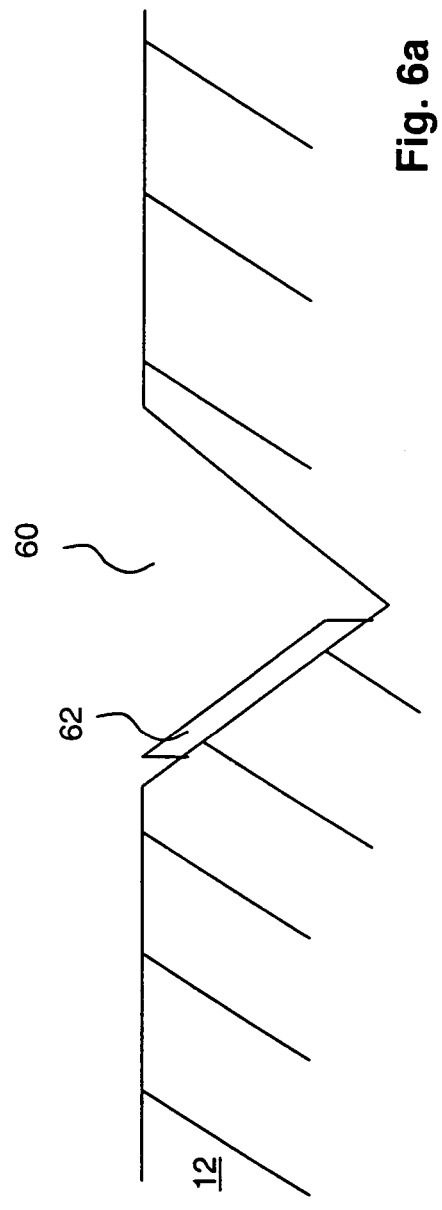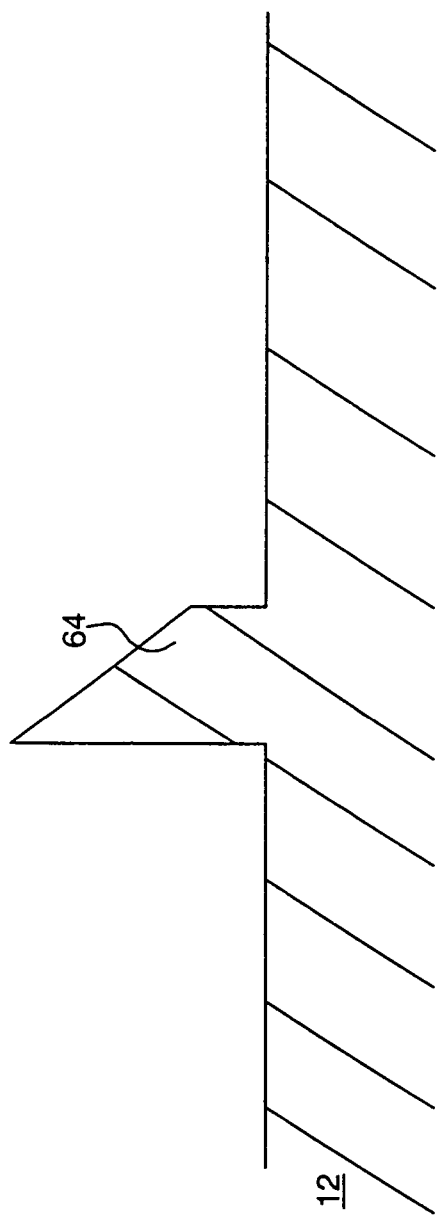

MEDICAL APPARATUS FOR DETERMINATION OF BIOLOGICAL CONDITIONS USING IMPEDANCE MEASUREMENTS

FIELD OF THE INVENTION

The present invention generally relates to the field of diagnosis of biological conditions, and in particular to a medical apparatus, electrodes for use in such a apparatus, micro structures for use in such electrodes, and a method for non-invasively diagnosing a diseased condition of the skin of a subject, particularly the presence of skin cancer, e.g. basal cell carcinoma or malignant melanoma, a squamous cell carcinoma or precursors thereof, using skin impedance measurements.

BACKGROUND OF THE INVENTION

Basal cell carcinoma (BCC) is the most common skin cancer. Its incidence is increasing in many countries throughout the world, for example, in Sweden. Long-term immunosuppression, e.g. after allogeneic organ transplantation, increases the risk of developing BCC and other skin tumours. This is also the case following exposure to ultraviolet light or ionizing radiation. There seems to be no apparent genetic connection and in many patients no other predisposing factors are found. However, clinical diagnosis of skin tumours can prove difficult even for experienced dermatologists, especially in the case of pigmented lesions. In the clinic there is a need for a diagnostic aid besides the established naked eye in combination with skin biopsies for histological examination.

Non-invasive methods of making biological determinations, such as clinical diagnosis of skin tumours, are generally desirable over invasive techniques that involve the taking of samples. Non-invasive techniques can be more convenient, e.g. less painful, involve less risk of infection etc. Accordingly, a number of non-invasive techniques for making biological determinations have been proposed:

| Application No. | Publication No | Publication date | Name |
|---|---|---|---|
| | U.S. Pat. No. 5,036,861 | Aug. 6, 1991 | Sembrowich et al. |
| | U.S. Pat. No. 5,115,133 | May 19, 1992 | Knudson |
| | U.S. Pat. No. 5,146,091 | Sep. 8, 1992 | Knudson |
| | U.S. Pat. No. 5,197,951 | Jan. 19, 1993 | Knudson. |
| | U.S. Pat. No. 5,222,496 | Jun. 29, 1993 | Clarke et al. |
| PCT/US94/08816 | WO95/04496 | Feb. 16, 1995 | Solid State Farms, inc. |
| | U.S. Pat. No. 5,433,197 | Jul. 18, 1995 | Stark |
| PCT/US97/13267 | WO 98/04190 | Feb. 5, 1998 | Dermal Therapy (Barbados) Inc. |
| PCT/US98/02037 | WO 99/39627 | Aug. 12, 1999 | Dermal Therapy (Barbados) Inc. |
| PCT/IB00/01464 | WO 01/26338 | Oct. 13, 2000 | Süsstrunk, et al. |

However, all of the above-mentioned documents disclose techniques for evaluating blood glucose levels and are consequently not suitable for diagnosing a diseased condition of the skin of a subject, particularly the presence of skin cancer, e.g. basal cell carcinoma.

Electrical impedance has been found to constitute a very sensitive indicator of minute changes in organic and biological material and especially tissues such as mucous membranes, skin and integuments of organs and, hence, provides an effective tool for non-invasive measurements of variations in structural properties of the tissue. In PCT/SE91/00703 a device for non-invasive measurement of electrical impedance of organic and biological material is disclosed. A probe comprising a number of electrodes arranged in a concentric ring system. The electrodes are driven from a control unit in such a way that the electric current path defining the actual tissue under test is dependent upon a control signal, is pressed towards the surface of the body part under test. By varying the control signal it is possible to select the region under test. Two rings supply voltage and the relation between the two will generate a virtual projection point located between the two rings. By adjusting the voltage relation between the two injection points the virtual injection point can be moved back and forth and hence the depth penetration in the tissue is selectable. However, human skin is a complex, heterogeneous, and anisotropic multilayer structure with electronically non-linear properties. The most non-linear properties are located to the Stratum Corneum (the outermost layer of epidermis). Therefore, there is information in all depth measurements that cannot be calculated by interpolation or extrapolation from two depths although the different depths are highly correlated. However, the device disclosed in PCT/SE91/00703 is impaired with a severe drawback in that it cannot deliver reliable results regarding tissue variation in skin layers beneath stratum corneum where, for example, skin cancer and allergic reactions manifest. This is due to the fact that non-invasive electrical impedance spectra of skin are dominated by the dielectric properties of the Stratum Corneum, especially at low frequencies. The stratum corneum has properties (a large and broad so called alpha dispersion) that may lead to that responses from underlying viable skin layers is confounded with responses from stratum corneum, thus diluting the clinically relevant information from the viable skin. This makes it difficult and unpredictable to assess electrical impedance phenomena that manifest below the stratum corneum using the probe disclosed in PCT/SE91/00703.

WO 01/52731 discloses a medical electrode for sensing electric biopotentials created within the body of a living subject. The electrode comprises a number of micro-needles adapted to penetrate the skin. The micro-needles are long enough to reach the stratum germinativum and are electrically conductive on their surface and connected to each other to form an array. According to WO 01/52731, the micro-needles are "nail-like", i.e. they have stem having a substantially circular cross-section with a constant or a gradually decreasing diameter and a tip-portion with a substantially spherical or needle-shaped tip. In EP 1 437 091 an apparatus for diagnosis of biological conditions using impedance measurements of organic and biological material is disclosed. The apparatus comprises a probe including a plurality of electrodes, where each electrode is provided with a number of micro-needles each having a length being sufficient to penetrate stratum corneum. The micro-needles according to EP 1 437 091 are also "nail-like", i.e. they have stem having a substantially circular cross-section with a constant or a gradually decreasing diameter and a tip-portion with a substantially spherical or needle-shaped tip.

However, practical experience has shown that electrodes furnished with micro-needles according to the conventional technique requires a substantial force or requires a significant manipulating, for example, tilting the electrode to and fro, in order to obtain a proper penetration of the micro-needles into the stratum germinativum. This may be uncomfortable and cumbersome for the patient as well as for the operator, e.g. a physician or a nurse, performing the test. Moreover, this may also require that the needles are construed with a sufficient strength by increasing its size in order to avoid the possibility of needle breakage during use.

Thus, there is a need of an improved medical electrode, apparatus for a non-invasively diagnosing a diseased condition of the skin of a subject, particularly the presence of skin cancer, e.g. basal cell carcinoma or malignant melanoma, a squamous cell carcinoma or precursors thereof.

BRIEF DESCRIPTION OF THE INVENTION

Thus, an object of the present invention is to provide an improved apparatus, an electrode device for use in such a apparatus, a micro structure for use in such an electrode, and a method for diagnosing a diseased condition of the skin of a subject, particularly the presence of skin cancer, e.g. basal cell carcinoma or malignant melanoma, a squamous cell carcinoma or precursors thereof in an accurate and reliable way.

It is another object of the present invention to provide an improved apparatus and a probe for use in such an apparatus for diagnosing a diseased condition of the skin of a subject having micro-needles with a good penetration ability.

It is a further object of the present invention to provide an improved apparatus and a probe for use in such an apparatus for diagnosing a diseased condition of the skin of a subject having micro-needles with a high structural strength.

It is yet another object of the present invention to provide an improved apparatus and a probe for use in such an apparatus for diagnosing a diseased condition of the skin of a subject having micro-needles with good electrical characteristics.

Still another object of the present invention is to provide micro-needles for an apparatus and a probe for use in such an apparatus for diagnosing a diseased condition of the skin of a subject that can be manufactured in an efficient and reliable way.

These and other objects are achieved according to the present invention by providing a medical apparatus and a method having the features defined in the independent claim. Preferable embodiments of the invention are characterised by the dependent claims.

According to an aspect of the present invention, there is provided a medical apparatus for the diagnosing of a diseased condition of the skin of a subject, comprising an electrically conducting probe including a plurality of electrodes, each electrode comprising a plurality of micro-needles, wherein the probe is adapted to be placed against a surface of the subject such that the micro-needles penetrate the stratum corneum, wherein the medical apparatus is adapted to initiate an impedance measurement session including passing an electrical current through the electrodes to obtain values of skin impedance, and use reference data to determine whether the obtained impedance values indicate the diseased condition. Each electrode comprises a base substrate, the micro-needles being integrally formed with the substrate and arranged in a laterally spaced relationship apart from each other and having a length being sufficient to penetrate the stratum corneum, the micro-needles being arranged with an at least partially oblique shape.

According to a second aspect of the present invention, there is provided an electrode adapted to be placed against a skin surface of a subject for the diagnosing of a diseased condition of the skin of the subject, comprising a plurality of micro-needles. The electrode comprises a base substrate, the micro-needles being integrally formed with the substrate and arranged in a laterally spaced relationship apart from each other and having a length being sufficient to penetrate the stratum corneum when placed against the skin surface of the subject, the micro-needles being arranged with an at least partially oblique shape.

According to third aspect of the invention, there is provided an array of micro-structures comprising: a base substrate; an array of simultaneously formed micro-needles projecting from a surface of the surface; wherein the micro-needles are arranged in a laterally spaced relationship apart from each other and having a length being sufficient to penetrate the stratum corneum when placed against a skin surface of a subject, the micro-needles being arranged with an at least partially oblique shape.

According to a further aspect of the present invention, there is provided a method for diagnosing a diseased condition of the skin of a subject, comprising the steps of: placing an electrically conducting probe against a skin surface of the subject such that micro-needles of the probe penetrate the stratum corneum, the micro-needles being integrally formed with a substrate and arranged in a laterally spaced relationship apart from each other and having a length being sufficient to penetrate the stratum corneum, wherein the micro-needles being arranged with an at least partially oblique shape; passing an electrical current through the electrodes to obtain values of skin impedance; and using reference data to determine whether the obtained impedance values indicate the diseased condition.

Thus, the invention is based on the insight that the non-invasive electrical impedance spectra of skin are dominated by the dielectric properties of the Stratum Corneum, especially at low frequencies. The stratum corneum has properties (a large and broad so called alpha dispersion) that may lead to that responses from underlying viable skin layers is confounded with responses from stratum corneum, thus diluting the clinically relevant information from the viable skin. In particular, the present invention is based on the design of the micro-needles with respect to a high degree of structure strength, good electric performance (e.g. with respect to conduction performance), and penetration ability.

This invention provides several advantages. One advantage is that electrical impedance phenomena that manifest below the stratum corneum can be assessed in a reliable manner using the present invention. Thereby, by using the present invention, a diseased condition of the skin of a subject, particularly the presence of skin cancer, e.g. basal cell carcinoma or malignant melanoma, a squamous cell carcinoma or precursors thereof can be diagnosed in an accurate and reliable way.

Another advantage is that the electrodes according to the present invention require less pressure than conventional electrodes to penetrate the stratum corneum. Thereby, the electrodes according to the invention is less dependent on the applied pressure, and hence less operator dependent. This also entails significantly less inconvenience for the patient or person subjected for the test in comparison with tests performed with the conventional electrodes.

A further advantage is that the micro-needles of the electrodes according to the present invention has a high degree of structural strength, that is, the needles are durable.

Yet another advantage is that the contact surface of a micro-needle according to the present invention against the skin of the subject can be made large leading to a good conduction between the needle and the stratum corneum, which, in turn, entails that the impedance can be measured with a high degree of accuracy and reliability.

According to an embodiment of the present invention, each micro-needle is arranged with a tip portion having an at least partially oblique shape. This particular design has been found to have a good penetration ability. Thereby, the electrodes will be less dependent on the applied pressure, and hence less operator dependent, which also entails less inconvenience for the person subjected for the test in comparison with tests performed with the conventional electrodes.

In a further embodiment, the micro-needles are arranged with a tip portion having an at least partially oblique end surface.

In yet another embodiment, each of the micro-needles is arranged with a substantially triangular cross-section. This design has been found to have a high degree of structure strength and a high penetration ability. Moreover, it has a large contact surface against the skin of the subject. This leads to a good conduction between the needle and the stratum corneum, which, in turn, entails that the impedance can be measured with a high degree of accuracy and reliability.

According to alternatives, each of the micro-needles is arranged with a substantially rombic, square-like, elliptical, polygonal, rectangular or circular cross-section.

In accordance with an embodiment of the present invention, the electrode arrays are arranged on a cap which can be removably attached to a probe for disposable use. Thus, after the measurements have been performed on a subject, the cap comprising the electrodes can be removed and thrown away and a new cap can be attached to the probe. Accordingly, the test can be made under hygienic conditions.

In an embodiment, the base substrate is formed from a wafer element and wherein the micro-needles are fabricated from the wafer element by a process comprising a consecutive sequence of an anisotropic etching process, a masking process, and deep reactive ion etching (DRIE) process on the substrate. This manufacturing process gives micro-needle arrays having a high degree of structure strength and the process also has a high yield.

According to a further embodiment of the present invention, the micro-needles of a first electrode and a second electrode is laterally spaced apart a first distance from each other and the micro-needles of the first and a third electrode is laterally spaced apart a second distance from each other, wherein a proportion of a potential between the first and the second electrode and the first and the third electrode is changed stepwise or gradually to obtain first and second values of skin impedance or a mixture of values of skin impedance between values obtained using the first and second electrode and values obtained using the first and third electrode. Thereby, the depth at which measurements are being performed can be selected in an accurate and reliable way.

In addition, the present invention may be used for measuring and/or monitoring and/or detecting biological conditions, for example, changes of skin properties of a subject, or changes of tissue properties of a subject. Moreover, the present invention may also be used for measuring and/or monitoring and/or detecting biological conditions of tissue of an organ, such as a kidney.

According to an embodiment of the present invention, the electrodes are shaped as rectangular bars. In accordance with alternatives, other configurations compatible with the essential features may also be conceivable. For example, the electrodes may be designed as C-shaped or concentric. Additional electrodes carrying guard, signal ground, driven guard, etc. may also be arranged. Cabling and shielding may be arranged in accordance with established engineering practice in order to minimize electromagnetic interference. Moreover, the design may also be adapted to conform to local safety regulations.

The features that characterize the invention, both as to organization and to method of operation, together with further objects and advantages thereof, will be better understood from the following description used in conjunction with the accompanying drawings. It is to be expressly understood that the drawings is for the purpose of illustration and description and is not intended as a definition of the limits of the invention. These and other objects attained, and advantages offered, by the present invention will become more fully apparent as the description that now follows is read in conjunction with the accompanying drawings.

BRIEF DESCRIPTION OF THE DRAWINGS

In the following detailed description, reference will be made to the accompanying drawings, of which:

FIG. 1a schematically shows a side view of an embodiment of a micro-needle for use in an electrode according to the present invention;

FIG. 1b schematically shows a top view of the micro-needle for use in an electrode according to the present invention shown in FIG. 1a;

FIG. 2a schematically shows a side view of another embodiment of a micro-needle for use in an electrode according to the present invention;

FIG. 2b schematically shows a top view of the micro-needle for use in an electrode according to the present invention shown in FIG. 2a;

FIG. 3a schematically shows a side view of an etched wafer during a manufacturing of micro-needles according to an embodiment of the present invention;

FIG. 3b schematically shows a top view of the etched wafer in FIG. 3a during a manufacturing of micro-needles according to the present invention;

FIG. 4a schematically shows a side view of an etched wafer provided with a masking layer;

FIG. 4b schematically shows a side view of the needle resulting from the masking layer in FIG. 4a;

FIG. 6a schematically shows a side view of an etched wafer provided with a masking layer;

FIG. 6b schematically shows a side view of the needle resulting from the masking layer in FIG. 6a;

FIG. 7b shows a procedure for attaching the removable cap comprising electrodes furnished with micro-needles according to the present invention on the probe shown in FIG. 7a;

FIG. 7c shows a procedure for attaching the removable cap comprising electrodes furnished with micro-needles according to the present invention on the probe shown in FIG. 7a;

FIG. 7d shows a procedure for attaching the removable cap comprising electrodes furnished with micro-needles according to the present invention on the probe shown in FIG. 7a;

DETAILED DESCRIPTION OF THE INVENTION

Figures 5C, 5F:
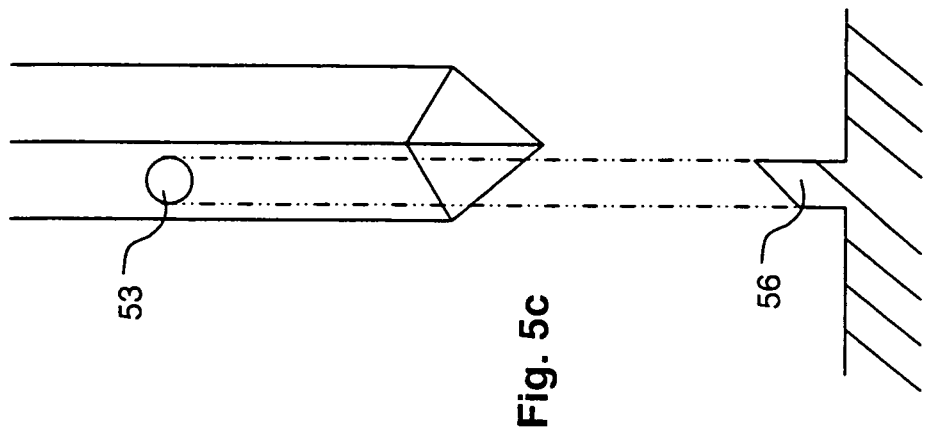
FIG. 5c schematically shows a top view of a ridge produced by an anisotropic etching process provided with a third mask configuration.
FIG. 5f schematically shows a side view of a needle obtained by the third mask configuration.

The probe according to the present invention includes a number of electrodes, at least three, and in the present invention each electrode is provided with at least one micro-needle, thereby forming a micro-needled surface, which permits measurements to be made at a variety of skin depths. The probe includes three rectangular areas or bars, each bar containing an array of 57 (19×3) micro-needles. Each bar is 1 mm wide and 5 mm long. The distance between the closest bars is 0.2 mm, and the distance between the second and the third bars is 1.8 mm. The active part of the probe is thus about 5×5 mm. Each micro-needle has a length of approximately 100 micrometer, as measured from its base, and a thickness of approximately 30 micrometer. The micro-needles are preferably made of silicon and covered with gold having a thickness of approximately 2 micrometer. Any material comprising a conductive surface with similar dimensions would work, but should be selected to be bio-compatible. The probe will be discussed in more detail hereinafter with reference to FIGS. 7a, 7b, 8a, and 8b.

With reference now to FIGS. 1a, 1b, 2a, and 2b, embodiments of micro structures or micro-needles for use in the above-mentioned electrode for the diagnosing of a diseased condition of the skin of a subject according to the present invention will be discussed. Only one micro-needle will be discussed in the following for the sake of simplicity, even though each electrode is provided with a plurality of such micro-needles arranged in arrays. A side view of an embodiment, i.e. a cross-sectional view of an embodiment along a plane perpendicular to the base substrate, and a top view of the embodiment, i.e. a cross-sectional view along a plane parallel to the substrate, are shown in FIG. 1a and FIG. 1b, respectively. A side view of another embodiment, i.e. a cross-sectional view of the embodiment along a plane perpendicular to the substrate, a top view of the embodiment, i.e. a cross-sectional view along a plane parallel to the substrate, are shown in FIG. 2a and FIG. 2b.

As mentioned above, each probe is provided with plurality of micro-needles, which micro-needles being integrally formed with the substrate and arranged in a laterally spaced relationship apart from each other and having a length being sufficient to penetrate the stratum corneum. Referring first to FIG. 1a, an embodiment of such a micro-needle according to the present invention is shown along a plane perpendicular to the substrate. A micro-needle 10 is arranged on a base substrate 12, for example, a silicon wafer of SOI type. The micro-needle 10 is arranged with inclined tip portion 14 or a tip portion having an at least partially oblique shape. The tip portion 14, i.e. the oblique surface, constitutes a part of the micro-needle 10. In FIG. 1b, a top view in the direction of the arrow indicated with B along a plane substantially parallel to substrate 12 in a cross-section of the micro-needle 10 indicated by A-A in FIG. 1a, i.e. at the base of the micro-needle, is shown. As can be seen, the micro-needle 10 has a triangular cross-section in this plane. The dimensions b1 and s1 of the micro-needle will be substantially constant along the height h1 and will taper continuously in a direction from the surface of the base substrate 12 along the height h2-h1. It should be noted that only a part of the substrate 12 is shown in FIG. 1b. Example dimensions with reference to FIGS. 1a and 1b are shown in table 1 below. With reference to FIGS. 2a and 2b, another embodiment of a micro-needle according to the present invention is shown along a plane perpendicular to the substrate. A micro-needle 20 is arranged on a base substrate 12, for example, a silicon wafer of SOI type. The micro-needle 20 is arranged with inclined tip portion 24 or a tip portion having an oblique shape. According to this embodiment, the tip portion 24 extends to the base substrate 12. In FIG. 2b, a top view in the direction of the arrow indicated with B along a plane substantially parallel to substrate 12 in a cross-section of the micro-needle 20 indicated by A-A in FIG. 2a, i.e. at the base of the micro-needle, is shown. As can be seen, the micro-needle 20 has a triangular cross-section in this plane. In this case, the cross-section parallel to the substrate 12 will taper continuously in a direction from the surface of the base substrate 12. It should be noted that only a part of the substrate 12 is shown in FIG. 2b. Example dimensions with reference to FIGS. 2a and 2b are also shown in table 1 below. For example, h1 is in the embodiment shown in FIG. 2a and FIG. 2b substantially zero.

TABLE 1

| Dimension | μm |
|---|---|
| h1 | 0-230 |
| h2 | 20-250 |
| w1 | 20-200 |
| b1 | 20-200 |
| s1 | 20-200 |

The fabrication of micro-needles extending from the plane of a silicon wafer is well known. See for example US 2004/0243063, "Microneedle array module and method for fabricating the same", Shuvo R., and Aaron J. F.; and U.S. Pat. No. 6,334,865, "Microneedle devices and methods for manufacture and use thereof", Allen M. G., et al.

The microneedle arrays according to the present invention may be formed from a wafer (a substrate), where inclined surfaces are provided on the substrate by an etching process, and a mask is provided on the inclined surfaces using an appropriate patterning process (such as lithography using photo resist). The structure of the needles are then formed in a desired configuration by a second etching process. The inclined surfaces enable the manufacture of needles having an oblique end surface at the tip portion of the needle.

The wafer-like substrate may be a single crystalline silicon having surfaces exhibiting crystal directions/orientations such as <100>, <110>, etc. However, other crystalline materials that can be subjected to the same or similar processing techniques are equally well suited. In particular, a useful starting substrate is so called SOI wafers (Silicon On Insulator), since SOI wafers will provide well defined etch stop layers. Such stop layers are practical for the purpose of defining dimensions (i.e. heights, widths, depths of recesses etc.) of the structures being made, and for eliminating certain unwanted side effects of etching.

Reference is now made to FIGS. 3a and 3b, FIG. 3a showing a side view of an etched wafer and FIG. 3b a top view of the same wafer. As mentioned above, an etching process to obtain the inclined surfaces 30 is first performed. Preferably, an anisotropic etching process, normally using aqueous KOH, is performed. This etching process will act on a silicon wafer 12 in which the <100> plane is horizontal, such that if a mask 34, that resists the etching medium, in the form of an elongated strip will provide a "ridge"-like structure having sloping/inclining side surfaces starting from under the mask and following the <111> plane at an angle of 54.7° down to the horizontal <100> plane. This is schematically shown in FIGS. 3a and 3b. The height of the pyramidal structure will depend on the etching, for example, the etching time. If an SOI wafer with a well defined Si thickness is used, the height can be controlled very accurately, since the oxide layer will act as an etch stop.

Referring now to FIGS. 4a, 4b and 5a-5f, FIG. 4a showing a side view of an etched wafer provided with a masking layer and FIG. 4b showing a side view of the resulting needle. FIGS. 5a-5f show different mask configurations for forming needles having different structures and the resulting needle structures. As can be seen in FIG. 4a, the inclined surfaces 40 are patterned in order to define the final structures, i.e. needles having an oblique tip surface. A lithographic procedure is utilized to provide a uniformly thick masking layer 42 on an inclined surface 40. For example, a photo resist, suitably by a spraying technique in conventional manner (thus known per se), is applied such that the entire surface is covered, which is then exposed to light such that only the desired mask portions defining the structures to be made will cure 44. Thereafter, the remaining portions of resist that has not cured will be removed by dissolving/washing. The resist is shown schematically in FIG. 4a before removing the uncured portions.

An isotropic etching procedure is then performed. A preferred procedure is a Deep Reactive Ion Etching (DRIE). Thus, the result will not depend on crystal plane orientation, and, therefore, the mask will define vertical walls of the protruding structure. The opposite inclined surface, i.e. the surface that is masked to yield a protruding structure, will remain as an inclined surface, by virtue of the DRIE being isotropic. The resulting needle 46 is shown in FIG. 4b. The mask 44 has not been removed yet in FIG. 4b.

Figures 5B, 5E:
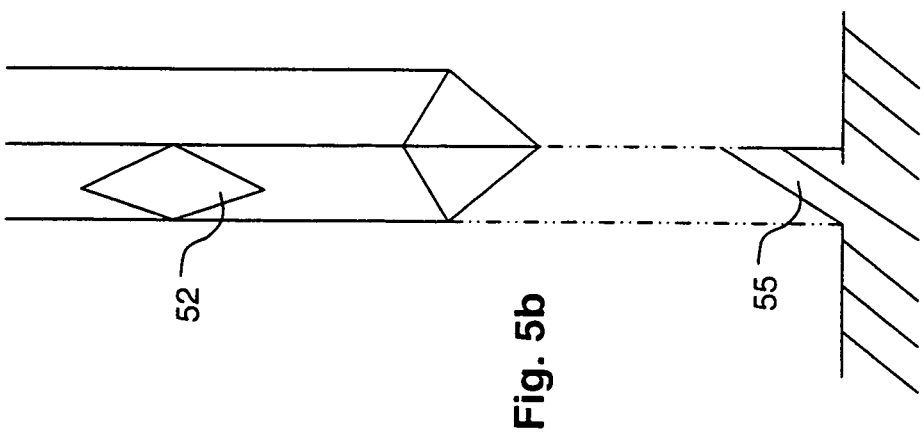
FIG. 5b schematically shows a top view of a ridge produced by an anisotropic etching process provided with a second mask configuration.
FIG. 5e schematically shows a side view of a needle obtained by the second mask configuration.
Figures 5A, 5D:
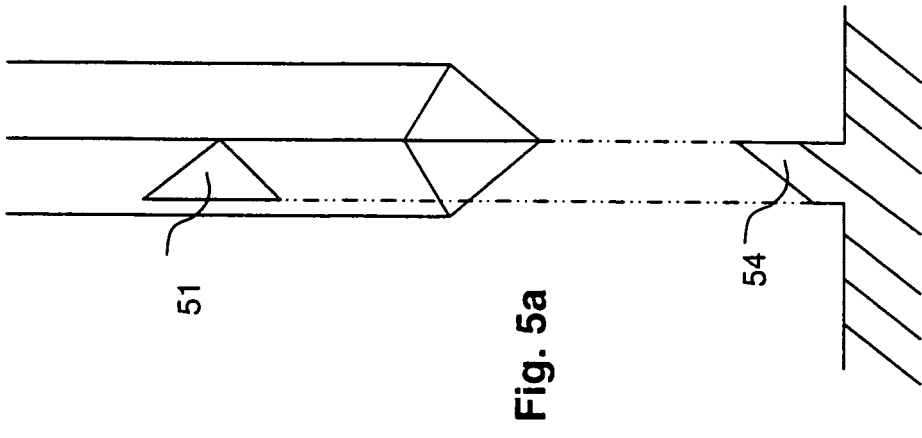
FIG. 5a schematically shows a top view of a ridge produced by an anisotropic etching process provided with a first mask configuration.
FIG. 5d schematically shows a side view of a needle obtained by the first mask configuration.

As can be seen in FIGS. 5a-5f, needles having a plurality of different shapes can be formed using this method, for example, triangular, circular, square, elliptical, polygonal, etc. In FIGS. 5a-5c, top views of the ridges provided with cured masks 51, 52, and 53, respectively. In FIGS. 5d-5e, side views of the resulting needles are shown, where a triangular needle 54 having an oblique tip portion is shown in FIG. 5d, a rhombic needle 55 having an oblique tip portion is shown in FIG. 5e, and a circular needle having an oblique tip portion is shown in FIG. 5f.

In an alternative embodiment of the above described method, the starting substrate for making protruding structures with obliquely shaped tip portions comprises V-shaped recesses 60 in the wafer instead of the protruding "ridges" discussed above, see FIG. 6a.

These recesses are made by masking a starting wafer so as to leave elongated slits in the resist, i.e. a "negative" of the mask from the first embodiment. Subsequently, this masked wafer is subjected to an anisotropic etch, for example, a KOH-etch, which will act selectively on the exposed wafer material through the slits, thereby yielding a V-groove 60 wherein the inclined surfaces correspond to the <111> planes of the crystalline wafer. Similarly to the above discussed embodiment, the wafer, now comprising a plurality of V-grooves, is appropriately masked, suitably using a resist that is sprayed on for achieving a uniform layer of resist, to define the geometry of the desired structure, analogously to the first embodiment. In FIG. 6a the cured mask portions 62 defining the desired needle is shown. A DRIE etch follows whereby wafer material is etched away to form vertically protruding structures, e.g. needles 64.

Alternative fabrication processes employing the SOI wafer approach as discussed above is the subject matter of a copending Swedish patent application (Title: "Micro needles and applications") filed on the same day as the present application in the name of Silex AB. Also, further details of the above-described fabrication method is the subject matter of the copending Swedish patent application (Title: "Micro needles and applications") filed on the same day as the present application in the name of Silex AB.

Figure 7A:
FIG. 7a shows an embodiment of a probe including electrodes furnished with micro-needles according to the present invention arranged on a removable cap.
Figure 7C:
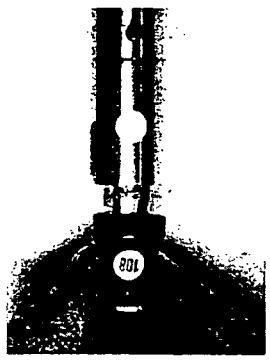
Figure 7B:
Figure 7D:
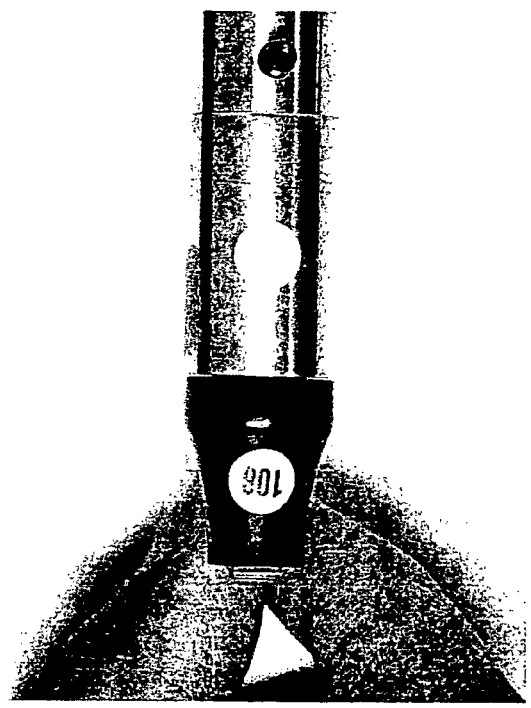

Turning now to FIGS. 7a-7d, an embodiment of a probe including a removable cap provided with electrodes according to the present invention. The probe includes a number of electrodes, at least three, and each electrode has a spiked surface, i.e. a surface provided with an array of microneedles in accordance with, for example, the needles discussed above with reference to FIGS. 1 and 2, which permits measurements to be made at a variety of skin depths. According to the embodiment shown in FIG. 7a, the probe includes three rectangular areas or bars each bar containing an array of 57 (19×3) needles. However, as the skilled man realizes, the probe may include other configurations of bars or areas containing other array configurations, for example, 51 (17×3), 24 (2×12), 60 (12×5), or 39 (13×3) needles. In FIGS. 7b-7d, it is shown how the removable electrode cap is attached to the probe. Thus, after the measurements have been performed on a subject, the cap comprising the electrodes can be removed and thrown away and a new cap can be attached to the probe and, accordingly, the test can be made under hygienic conditions.

Figure 8A:
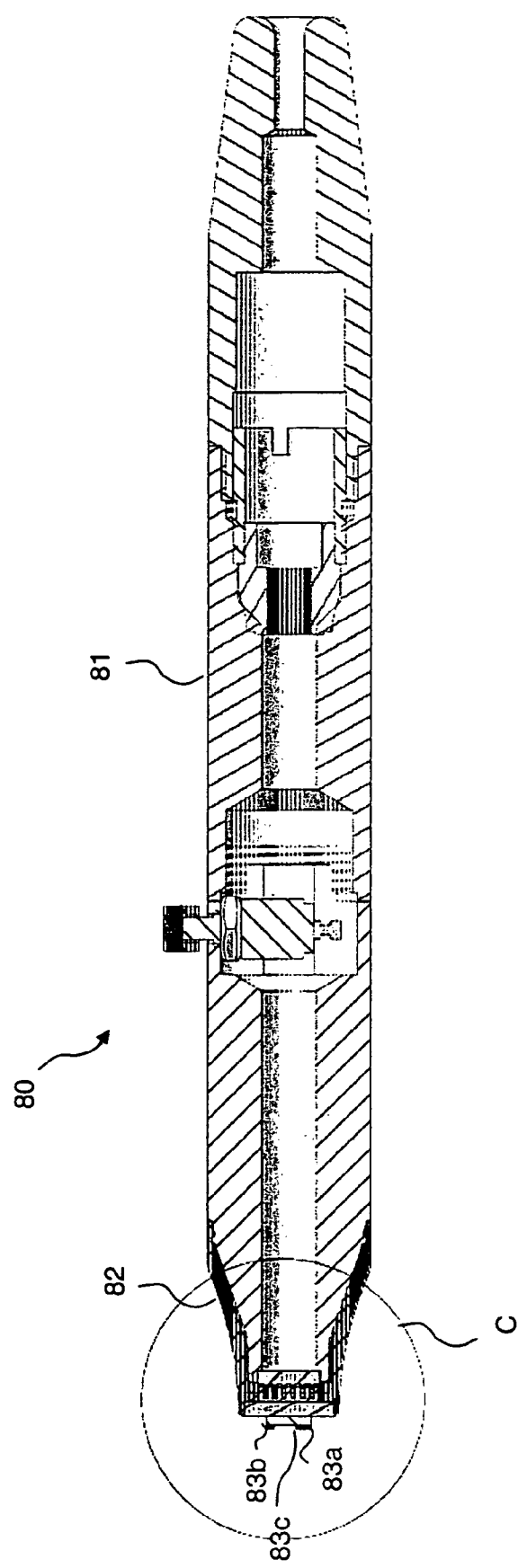
FIG. 8a shows a cross-section of probe including electrodes furnished with micro-needles according to the present invention arranged on a removable cap.
Figure 8B:
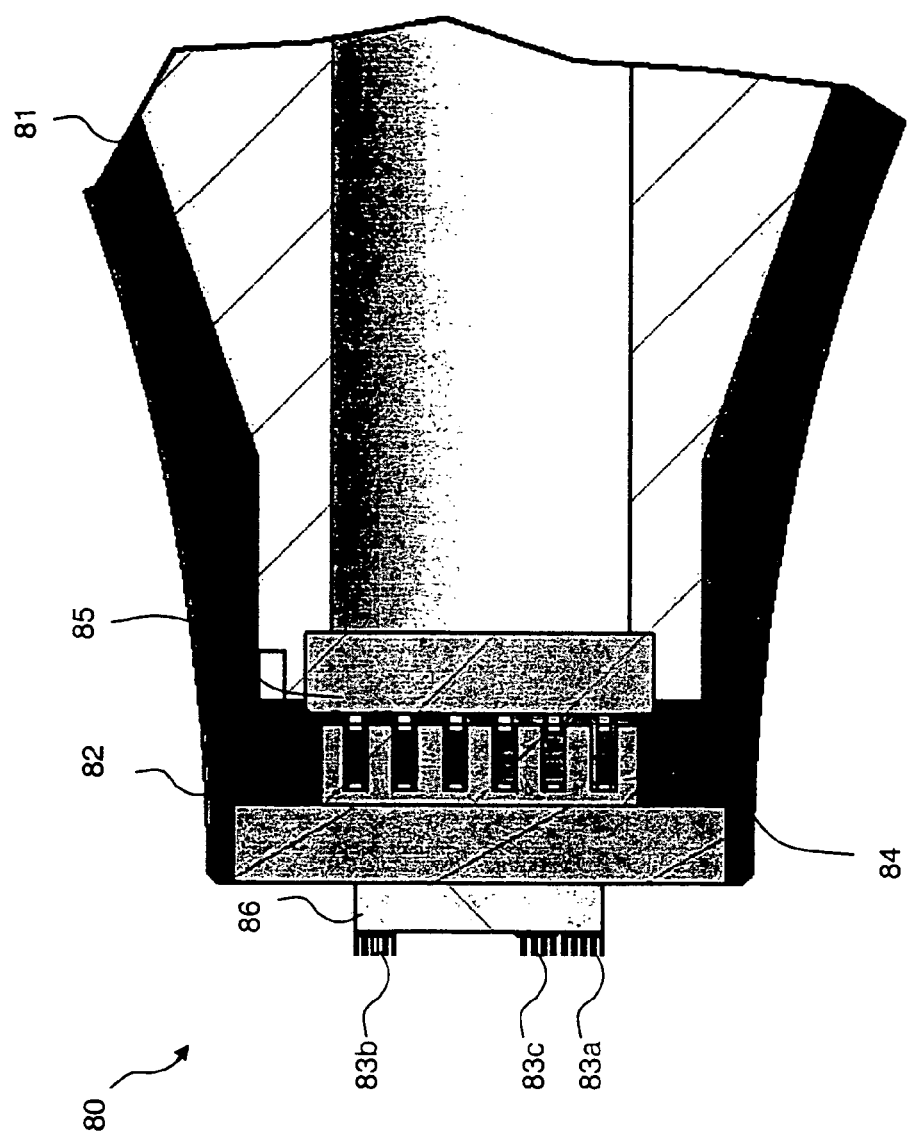
FIG. 8b is an enlarged view of cap shown in FIG. 8a in cross-section.

In FIG. 8a the probe shown in FIG. 7a-7d is shown in cross-section and FIG. 8b is an enlarged view of the encircled portion C in FIG. 8a. The probe 80 comprises a housing 81, preferably made of a metal such as steel or another durable material, which also functions as a handle or shaft during use, for example, during measurements when the operator presses the electrode against the skin of a subject. A removable cap 82 can be releasable attached to an end of the probe 80, which is shown in FIGS. 7b-7d. Preferable, the cap 82 is made of a material such as plastic, which enables a user of the probe to thread the cap 82 on the tip portion of the housing 81. The removable cap 82 is provided with electrodes 83a-83c arranged on a base substrate 86. In this embodiment, three electrodes 83a-83c each comprising an array of 57 (19×3) micro-needles is arranged on the cap 82. The cap 82 is disposable for hygienic reasons. Furthermore, as can be seen in FIG. 8b, the cap 82 comprises connection means 84 including terminals, in this case six terminals, adapted to make contact with corresponding connection means 85 including terminals arranged in the housing 81, in this case six terminals, of the probe 80 when the cap 82 is fully attached to the probe 80. Thereby, the electrodes 83a-83c of the cap 82 can be supplied with electrical current.

In FIGS. 8a and 8b, the electrodes 83a-83c are shaped as rectangular bars but, as the skilled man in the art realizes, other topological shapes compatible with the essential features are also conceivable. For example, the electrodes may be designed as C-shaped or concentric. Additional electrodes carrying guard, signal ground, driven guard, etc. may also be arranged. Cabling and shielding may be arranged in accordance with established engineering practice in order to minimize electromagnetic interference. Moreover, the design may also be adapted to conform to local safety regulations.

As discussed above, the micro-needles are laterally spaced apart from each other and having a length being sufficient to penetrate the stratum corneum. The probe is adapted to be placed against a skin surface of the subject such that the micro-needles penetrate the stratum corneum. Preferably, the skin surface sites are soaked prior to each impedance measurement using, for example, a 0.9% saline solution. The sites can be soaked, for example, for 60 seconds prior to the measurement.

The apparatus according to the present invention is adapted to pass an electrical current through the electrodes to obtain a spectrum/range of values of skin impedance and to use reference data to determine whether the obtained impedance value indicates the diseased condition. The electrical current has a frequency between about 10 Hz and about 10 MHz.

The apparatus without the micro-needled probe is known as the SciBase II depth selective spectrometer, may be obtained from SciBase AB of Stockholm, Sweden. The pin assignment for the probe connected may be as follows:
1. <START> button.
2. sense (first electrode illustrated in FIG. 8(*b*) indicated by reference numeral 83a; use coaxial (conventional probe) screen 3).
3. gnd (for sense).
4. near exciter (second (middle) electrode illustrated in FIG. 8(*b*) indicated by reference numeral 83c; use coaxial (conventional probe) screen 5).
5. gnd (for near injection).
6. gnd.
7. far exciter (third (right-most) electrode illustrated in FIG. 8(*b*) indicated by reference numeral 83b; use coaxial (conventional probe) screen 8).
8. gnd (for far injection).
9. chassis.
10. reserved.
11. reserved.
12. gnd.
13. gnd.
14. charger.

Preferably, the impedance was measured using the SciBase II depth selective spectrometer at 35 logarithimically distributed frequencies from 1 kHz to 2.5 MHz at five depth settings. In this embodiment, ten frequencies per decade is used.

The signal is voltage driven signal and has a signal strength preferably within a range of 0-50 mV rms, i.e. below the resting potential of a living cell of a human being, which is approximately 70 mV.

Each micro-needle may be at least 20, or at least 30, or at least 40, or at least 50, or at least 60, or at least 70, or at least 80, or at least 90 μm in length. Additionally, each micro-needle may be up to 250, or up to 240, or up to 230, or up to 220, or up to 210, or up to 200, or up to 190, or up to 180, or up to 170, or up to 160, or up to 150, or up to 140, or up to 130, or up to 120, or up to 110, or up to 100 μm in length.

According to an alternative embodiment, each micro-needle has a thickness of about 30 micrometer.

According to the invention, the probe comprises three electrodes, wherein a first electrode and a second electrode being laterally spaced apart a first distance from each other and the first and a third electrode being laterally spaced apart a second distance from each other. This is illustrated in FIG. 8b, where the sense electrode 83a is spaced apart from the near exciter electrode 83c and the far exciter electrode 83b, respectively. The first distance and the second distance are different from each other. The first distance is between about 0.1 mm and about 40 mm and the second distance is between about 1 mm and about 50 mm. The apparatus is adapted to gradually or stepwise change a proportion of a potential between the first and the second electrode and the first and the third electrode to obtain first and second values of skin impedance. Specifically, the first distance is between about 0.1 mm and about 40 mm, or between about 0.1 mm and about 30 mm, or between about 0.1 mm and about 25 mm, or between about 0.1 mm and about 20 mm, or between about 0.1 mm and about 15 mm, or between about 0.2 mm and about 10 mm, or between about 0.2 mm and about 5 mm, or between about 0.2 mm and about 3 mm, or between about 0.2 mm and about 2 mm, or between about 0.2 mm and about 1.5 mm, or between about 0.2 mm and about 1 mm, or between about 0.2 mm and about 0.5 mm. In addition, the second distance is between about 1 mm and about 50 mm, or between about 1 mm and about 40 mm, or between about 1 mm and about 30 mm, or between about 1 mm and about 15 mm, or between about 1 mm and about 10 mm, or between about 1 mm and about 9 mm, or between about 1 mm and about 8 mm, or between about 1 mm and about 7 mm, or between about 2 mm and about 8 mm, or between about 3 mm and about 7 mm, or between about 4 mm and about 7 mm, or between about 4 mm and about 6 mm, or about 5 mm.

Furthermore, each electrode may comprise at least two micro-needles, or at least three micro-needles, or at least four micro-needles, or at least five micro-needles, or at least six micro-needles, or at least seven micro-needles, or at least eight micro-needles, or at least nine micro-needles, or at least ten micro-needles, or at least twelve micro-needles, or at least fifteen micro-needles, or at least eighteen micro-needles, or at least twenty micro-needles, or at least twenty-five micro-needles, or at least thirty micro-needles, or at least thirty-five micro-needles, or at least fifty micro-needles. As mentioned above, the probe illustrated in FIGS. 7 and 8 includes three rectangular areas or bars, each bar containing an array of 57 (19×3) micro-needles, but, as the skilled man realizes, a number of other array configurations, for example, arrays of 39 (13×3), 45 (15×3), 24 (12×2), 48 (4×12), 65 (13×5), or 51 (17×3) micro-needles are also conceivable. According to alternatives, the micro-needles are arranged in a non-linear fashion. Also electrodes having only one row of micro-needles are conceivable.

Impedance measurements using the probe according to the present invention of a subject suffering from basal cell carcinoma or malignant melanoma: at a first site of normal (unaffected skin); and at a second site of diseased skin, may be performed in accordance with the approach described in Emtestam I, Nicander I, Stenstrom M, Ollmar S. "Electrical impedance of nodular basal cell carcinoma: a pilot study", Dermatology 1998; 197: 313-316, and Kapoor S. "Bioelectric impedance techniques for clinical detection of skin cancer using simple electrical impedance indices", Skin Res Technol 2003; 9: 257-261, and Beetner D G, Kapoor S, Manjunath S, Zhou X, Stoecker W V "Differentation among basal cell carcinoma, benign lesions, and normal skin using electric impedance", IEEE Trans Biomed Eng 2003; 50: 1020-1025. However, the measurements described in these references were obtained using a conventional probe and an early version of the impedance spectrometer.

Figure 9A:
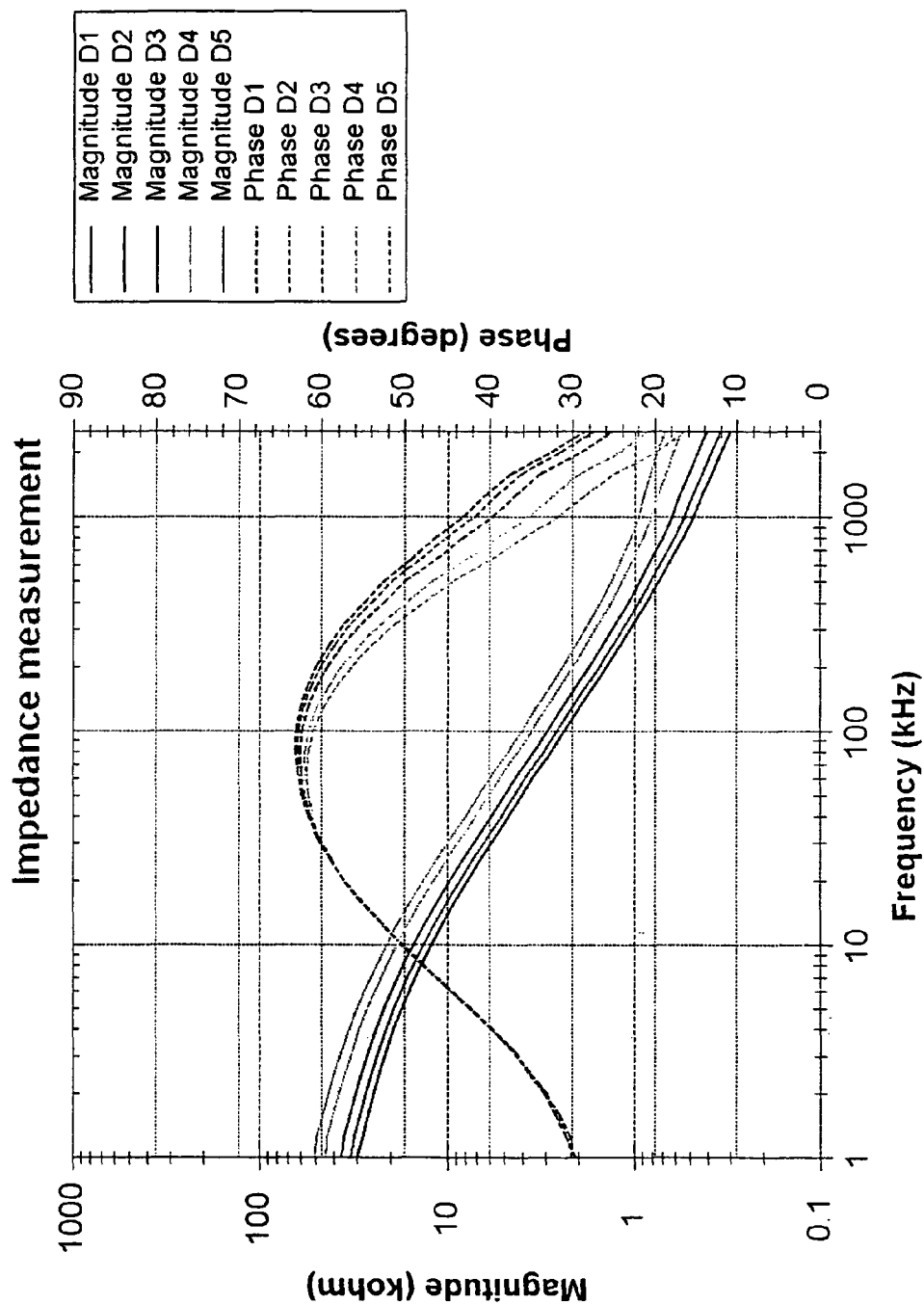
FIG. 9a shows a diagram of the results obtained by measurements at a first site of normal (unaffected skin), i.e. a reference site, using the probe according to the present invention.
Figure 9B:
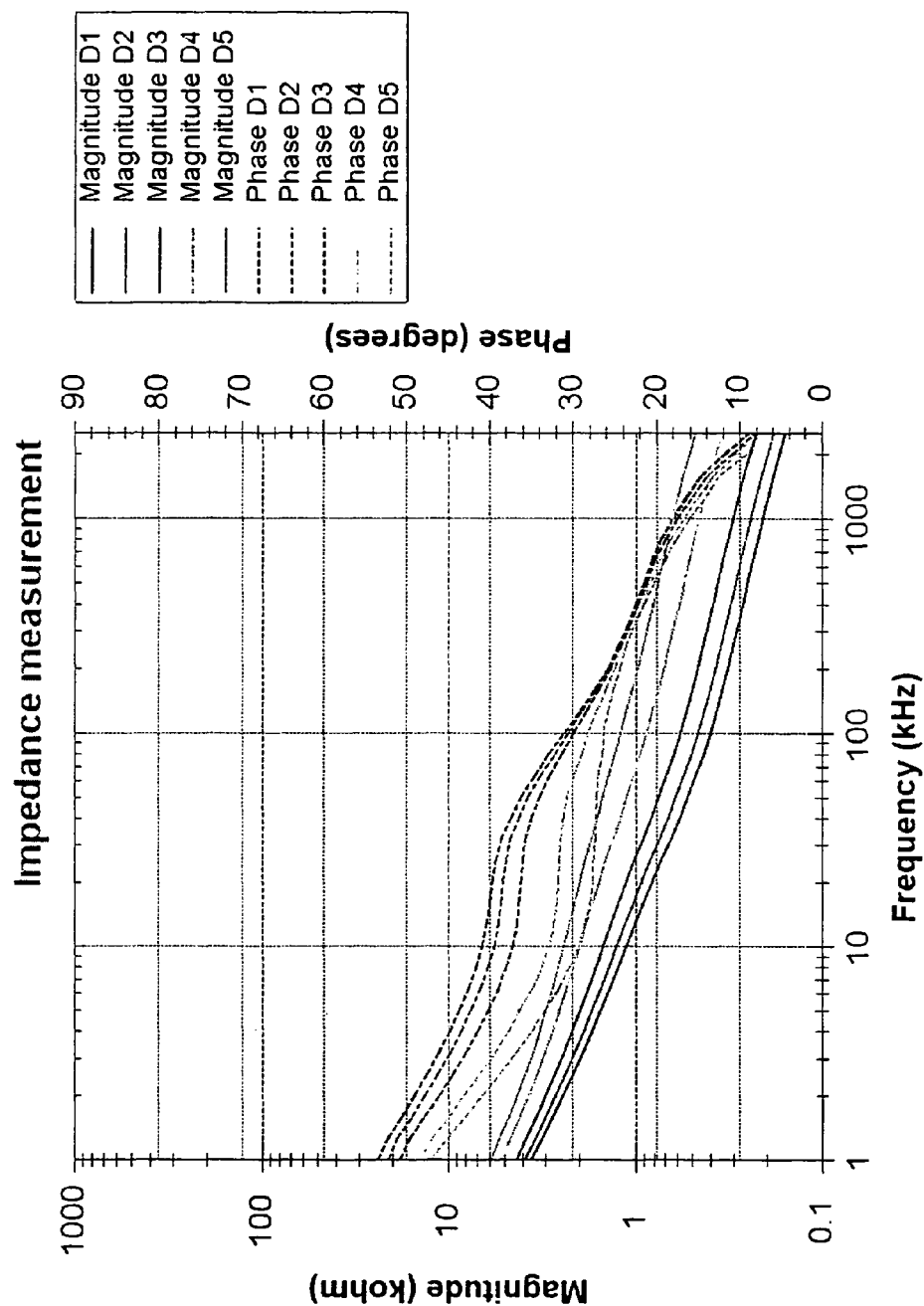
FIG. 9b shows a diagram of the results obtained by measurements at a second site of diseased skin using the probe according to the present invention.

In FIGS. 9a and 9b results from measurements performed using a probe with micro-needles designed in accordance with the embodiment described with reference to FIGS. 1a and 1b, i.e. with a triangular cross-section, of a subject suffering from basal cell carcinoma are shown. In FIG. 9a measurements at a first site of normal (unaffected skin), i.e. a reference site, and in FIG. 9b measurements at a second site of diseased skin, are shown, respectively. As can be seen, there is a significant deviation of the impedance, both with respect to the phase and the magnitude, between measurements performed on a site of unaffected skin and measurements performed on a site of diseased skin.

It is desirable to detect and remove skin cancers as early as possible. As such, precursors of skin cancer, such as, for example, actinic keratose (a precursor of squamous cell carcinoma) and dysplastic nevi (a precursor of malignant melanoma), as well as other lesions that may be mixed up with various cancers unless surgery and histological evaluation of the catch is made, can be detected using impedance measurements of the present invention in the manner described herein.

In addition, the present invention may be used for measuring and/or monitoring and/or detecting biological conditions, for example, changes of skin properties of a subject, or changes of tissue properties of a subject. Moreover, the present invention may also be used for measuring and/or monitoring and/or detecting biological conditions of tissue of an organ, such as a kidney.

Although exemplary embodiments of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting example thereof and that the scope of protection is defined by the appended patent claims.

The invention claimed is:

1. A medical apparatus for the diagnosing of a diseased condition of the skin of a subject, comprising:
an electrically conducting probe including a plurality of electrodes, each electrode comprising a base substrate and a plurality of micro-needles, wherein said probe is adapted to be placed against a surface of the subject such that said micro-needles penetrate the stratum corneum, wherein said medical apparatus is adapted to initiate an impedance measurement session including passing an electrical current through the electrodes to obtain values of skin impedance, and use reference data to determine whether the obtained impedance values indicate the diseased condition,
said micro-needles being integrally formed with said substrate and arranged in a laterally spaced relationship apart from each other and having a length being sufficient to penetrate the stratum corneum, said micro-needles having a triangular cross-section parallel to the base substrate along an entire length thereof, and said micro-needles being arranged with at least one oblique surface extending from a tip thereof to the base substrate such that the cross-section parallel to the base substrate tapers continuously along the entire length thereof from the base substrate to the tip, and
the triangular cross-section at the bottom of said micro-needles having two equal sides with a length of s1 and a third side with a length of b1, wherein s1 is between 20 μm and 200 μm, and b1 is between 20 μm and 200 μm.

2. The medical apparatus according to claim 1, wherein each of said micro-needles has a length being sufficient to penetrate below the skin surface to the Stratum Germinativum or through the Stratum Corneum into the living Epidermis but not into the Dermis.

3. The medical apparatus according to claim 1, wherein said medical apparatus is adapted to, at placing against a surface of an object, provide an indication that said micro-needles have penetrated below the skin surface to the Stratum Germinativum or through the Stratum Corneum into the living Epidermis but not into the Dermis.

4. The medical apparatus according to claim 3, wherein said medical apparatus is adapted to, at placing against a surface of an object, pass an electrical current having a frequency at a lower end of a predetermined frequency spectrum through the electrodes in order to obtain values of skin impedance, compare said obtained impedance values with a predetermined reference impedance value for said frequency and determine that said micro-needles have penetrated the stratum corneum if said obtained impedance value is below said reference value.

5. The medical apparatus according to claim 1, wherein the diseased condition is skin cancer.

6. The medical apparatus according to claim 5, wherein skin cancer is a basal cell carcinoma, a malignant melanoma, a squamous cell carcinoma, or precursors of such lesions.

7. The medical apparatus according to claim 1, wherein each micro-needle has a length of at least about 10 μm and a length up to about 250 μm.

8. The medical apparatus according to claim 1, wherein each micro-needle has a length of at about 100 μm.

9. The medical apparatus according to claim 1, wherein said probe comprises three said micro-needle furnished electrodes, the micro-needles of a first electrode and a second electrode being laterally spaced apart a first distance from each other and the micro-needles of the first and a third electrode being laterally spaced apart a second distance from each other, said apparatus being adapted to gradually change a proportion of a potential between the first and the second electrode and the first and the third electrode to obtain first and second values of skin impedance or a mixture of values of skin impedance between values obtained using the first and second electrode and values obtained using the first and third electrode.

10. The medical apparatus according to claim 9, wherein said first distance and said second distance are different from each other.

11. The medical apparatus according to claim 9, wherein said first distance is between about 0.1 mm and about 40 mm.

12. The medical apparatus according to claim 9, wherein said second distance is between about 1 mm and about 50 mm.

13. The medical apparatus according to claim 1, wherein said electrical current has a frequency in a predetermined frequency spectrum between about 10 Hz and about 10 MHz.

14. The medical apparatus according to claim 13, wherein said apparatus is adapted to pass said electrical current through the electrodes at a plurality of logarithmically distributed frequencies, said frequencies having a range from 1 kHz to 2.5 MHz.

15. The medical apparatus according to claim 1, wherein said electrodes are arranged on a removable cap adapted to be attached to said probe, said cap including connection means adapted to, when said cap is attached to the probe, supply said electrodes with electrical current.

16. A method for diagnosing a diseased condition of the skin of a subject, comprising the steps of:
    placing an electrically conducting probe against a skin surface of the subject, said probe being arranged in accordance with claim 1;
    passing an electrical current having a frequency at a lower end of a predetermined frequency spectrum through the electrodes to obtain values of skin impedance; and
    using reference data to determine whether the obtained impedance values indicate the diseased condition.

17. The medical apparatus according to claim 16, wherein the diseased condition is skin cancer.

18. The method according to claim 17, wherein skin cancer is a basal cell carcinoma, a malignant melanoma, a squamous cell carcinoma, or precursors of such lesions.

19. The method according to claim 16, wherein both non-invasive surface electrodes (conventional probes) are used in conjunction with said micro-needled electrodes to catch more aspects of skin properties in order to improve power of discrimination.

20. The method according to claim 16, wherein said probe comprises three said micro-needle furnished electrodes, the micro-needles of a first electrode and a second electrode being laterally spaced apart a first distance from each other and the micro-needles of the first and a third electrode being laterally spaced apart a second distance from each other, wherein said step of passing an electrical current further comprises the step of gradually changing a proportion of a potential between the first and the second electrode and the first and the third electrode to obtain first and second values of skin impedance or a mixture of values of skin impedance between values obtained using the first and second electrode and values obtained using the first and third electrode.

21. The method according to claim 16, wherein said electrical current has a frequency in a predetermined frequency spectrum between about 10 Hz and about 10 MHz.

22. The method according to claim 21, wherein said step of passing an electric current comprises the step of passing said electrical current through the electrodes at a plurality of logarithmically distributed frequencies, said frequencies having a range from 1 kHz to 2.5 MHz.

23. A non-transitory computer program product, which when executed on a computer, performs steps in accordance with claim 16.

24. A non-transitory computer readable medium comprising instructions for bringing a computer to perform steps in accordance with the method according to claim 16.

25. An electrode adapted to be placed against a skin surface of a subject for the diagnosing of a diseased condition of the skin of the subject, comprising:
    a base substrate and a plurality of micro-needles,
    said micro-needles being integrally formed with said base substrate and arranged in a laterally spaced relationship apart from each other and having a length being sufficient to penetrate the stratum corneum when placed against the skin surface of the subject, said micro-needles having a triangular cross-section parallel to the base substrate along an entire length thereof, and said micro-needles being arranged with at least one oblique surface extending from a tip thereof to the base substrate such that the cross-section parallel to the base substrate tapers continuously along the entire length thereof from the base substrate to the tip, and
    the triangular cross-section at the bottom of said micro-needles having two equal sides with a length of s1 and a third side with a length of b1, wherein s1 is between 20 μm and 200 μm, and b1 is between 20 μm and 200 μm.

26. The electrode according to claim 25, wherein each of said micro-needles has a length being sufficient to penetrate below the skin surface to the Stratum Germinativum or through the Stratum Corneum into the living Epidermis but not into the Dermis.

27. The electrode according to claim 25, wherein each micro-needle has a length of at least about 10 μm and a length up to about 250 μm.

28. The electrode according to claim 25, wherein each micro-needle has a length of at about 100 μm.

29. A removable cap adapted to be attached to an electrically conducting probe, said cap including at least three electrodes according to claim 25, and a connector adapted to, when said cap is attached to the probe, supply said electrodes with electrical current.

30. An array of micro-structures, comprising:
    a base substrate; and
    an array of simultaneously formed micro-needles projecting from a surface of said base substrate,
    wherein said micro-needles are arranged in a laterally spaced relationship apart from each other and having a length being sufficient to penetrate the stratum corneum when placed against a skin surface of a subject, said micro-needles having a triangular cross-section parallel to the base substrate along an entire length thereof, and said micro-needles being arranged with at least one oblique surface extending from a tip thereof to the base substrate such that the cross-section parallel to the base substrate tapers continuously along the entire length thereof from the base substrate to the tip, and
    wherein the triangular cross-section at the bottom of said micro-needles has two equal sides with a length of s1 and a third side with a length of b1, wherein s1 is between 20 μm and 200 μm, and b1 is between 20 μm and 200 μm.

31. The array of micro-structures according to claim 30, wherein said micro-needles have a length in a range of about 10 μm to about 250 μm to penetrate the Stratum Corneum into the living Epidermis but not into the Dermis.

* * * * *